(12) United States Patent
Kruse

(10) Patent No.: US 8,586,359 B2
(45) Date of Patent: Nov. 19, 2013

(54) COMPOSITIONS AND METHODS OF PREPARING ALLOREACTIVE CYTOTOXIC T CELLS

(75) Inventor: Carol A. Kruse, San Diego, CA (US)

(73) Assignee: Promising Furture, LLC, Hagatna, GU (US)

( * ) Notice: Subject to any disclaimer, the term of this patent is extended or adjusted under 35 U.S.C. 154(b) by 279 days.

(21) Appl. No.: 12/844,516

(22) Filed: Jul. 27, 2010

(65) Prior Publication Data

US 2011/0027244 A1 Feb. 3, 2011

Related U.S. Application Data

(60) Provisional application No. 61/229,233, filed on Jul. 28, 2009, provisional application No. 61/229,229, filed on Jul. 28, 2009.

(51) Int. Cl.
C12N 5/00 (2006.01)
C12N 5/02 (2006.01)

(52) U.S. Cl.
USPC ..................................................... 435/372.3

(58) Field of Classification Search
None
See application file for complete search history.

(56) References Cited

U.S. PATENT DOCUMENTS

| | | | | |
|---|---|---|---|---|
| 5,827,737 A * | 10/1998 | Peterson et al. | ............... | 435/348 |
| 6,316,257 B1 * | 11/2001 | Flyer et al. | ................ | 435/372.3 |
| 7,354,909 B2 * | 4/2008 | Klinman et al. | ............ | 514/44 R |
| 2011/0135617 A1 * | 6/2011 | Kruse | ........................ | 424/93.71 |

FOREIGN PATENT DOCUMENTS

WO    WO 97/22349    * 12/1996

OTHER PUBLICATIONS

Immunology of the Nervous System, edited by Robert W. Keane, Ph.D. and William F. Hickey, M.D., Oxford University Press (1997), pp. 99-133 (by J. Wayne Streilein and Andrew W. Taylor).
Immunology of the Nervous System, edited by Robert W. Keane, Ph.D. and William F. Hickey, M.D., Oxford University Press (1997), pp. 611-641 (by Maciej Poltorak and William J. Freed).
Immunology of the Nervous System, edited by Robert W. Keane, Ph.D. and William F. Hickey, M.D., Oxford University Press (1997), pp. 760-784 (by Carol J. Wikstrand and Darell D. Bigner).
Charles A Janeway, Jr. and Paul Travers, ImmunoBiology The Immune System in Health and Disease, Current Biology Ltd and Garland Publishing Inc, pp. 12:32-12:33 , 1997.
René J. Duquesnoy, HLA Matchmaker: A Molecularly Based Algorithm for Histocompatibility Determination. I. Description of the Algorithm, Human Immunology 63, 339-352 (2002).
René J. Duquesnoy, HLA Matchmaker: A Molecularly Based Algorithm for Histocompatibility Determination. II. Verification of the Algorithm and Determination of the Relative Immunogenicity of Amino Acid Triplet-Defined Epitopes, Human Immunology 63, 353-363 (2002).
Marlies K.A. Dankers, Martin B.A. Heemskerk, Rene J. Duquesnoy, Ilias I.N. Doxiadis, Machteld Oudshoorn, Dave L. Roelen, Frans H.J. Claas, HLAMatchmaker Algorithm is not a Suitable Tool to Predict the Alloreactive Cytotoxic T-Lymphocyte Response in vitro, Transplantation, vol. 78, No. 1, Jul. 15, 2004.
Carol A. Kruse and L. Tony Beck, Artificial-capillary-system development of human alloreactive cytotoxic T-lymphocytes that can lyse brain tumours, Biotechnol. Appl. Biochem. (1977), 25, 197-205 (Printed in Great Britain).
Carol A. Kruse, Linda Cepeda, Betty Owens, Stephen D. Johnson, John Stears, Kevin O. Lillehei, Treatment of recurrent glioma with intracavitary alloreactive cytotoxic T lymphocytes and interleukin-2, Cancer Immunol. Immunother. (1977), 45: 77-87.
Brain Tumor Immunotherapy, edited by L.M. Liau et al., Humana Press Inc., pp. 149-170 (Chapter 7), 1997.
Tavakoli, S. et al., Phenotype and function of monocyte derived dendritic cells in chronic hepatitis B virus infection, Gen. Virol., Oct. 2004, vol. 85 (Pt 10), pp. 2829-2836 (See Introduction and Methods).
Nishioka, Y. et al., Differential effects of IL-12 on the generation of allo-reactive CTL mediated by murine and human dendritic cells: a critical role for nitric oxide, J. Leukoc. Biol., May 2003, vol. 73, No. 5, pp. 621-629 (See Materials and Methods).
Specht, J.M. et al., Dendritic cells retrovirally transduced with a model antigen gene are therapeutically effective against established pulmonary metastases, J. Exp. Med., Oct. 20, 1997, vol. 186, No. 8, pp. 1213-1221 (See Materials and Methods).
Tosch, C. et al., Adenovirus-mediated gene transfer of pathogen-associated molecular patterns for cancer immunotherapy, Cancer Gene Ther., Apr. 2009, vol. 16, No. 4, pp. 310-319 (See Abstract).
Kronik. N. et al., Improving alloreactive CTL immunotherapy for malignant gliomas using a simulation of their interactive dynamics, Cancer Immunol. Immunother, Mar. 2008, vol. 57, No. 3, pp. 425-439 (See Abstract).

* cited by examiner

Primary Examiner — Michail Belyavskyi
(74) Attorney, Agent, or Firm — Themis Law; Franco A. Serafini; David M. Fortner

(57) ABSTRACT

Provided herein are compositions and methods of preparing therapeutic cytotoxic T cells. In certain embodiments, such T cells are generated through activation of donor cells by patient stimulator cells.

12 Claims, 1 Drawing Sheet

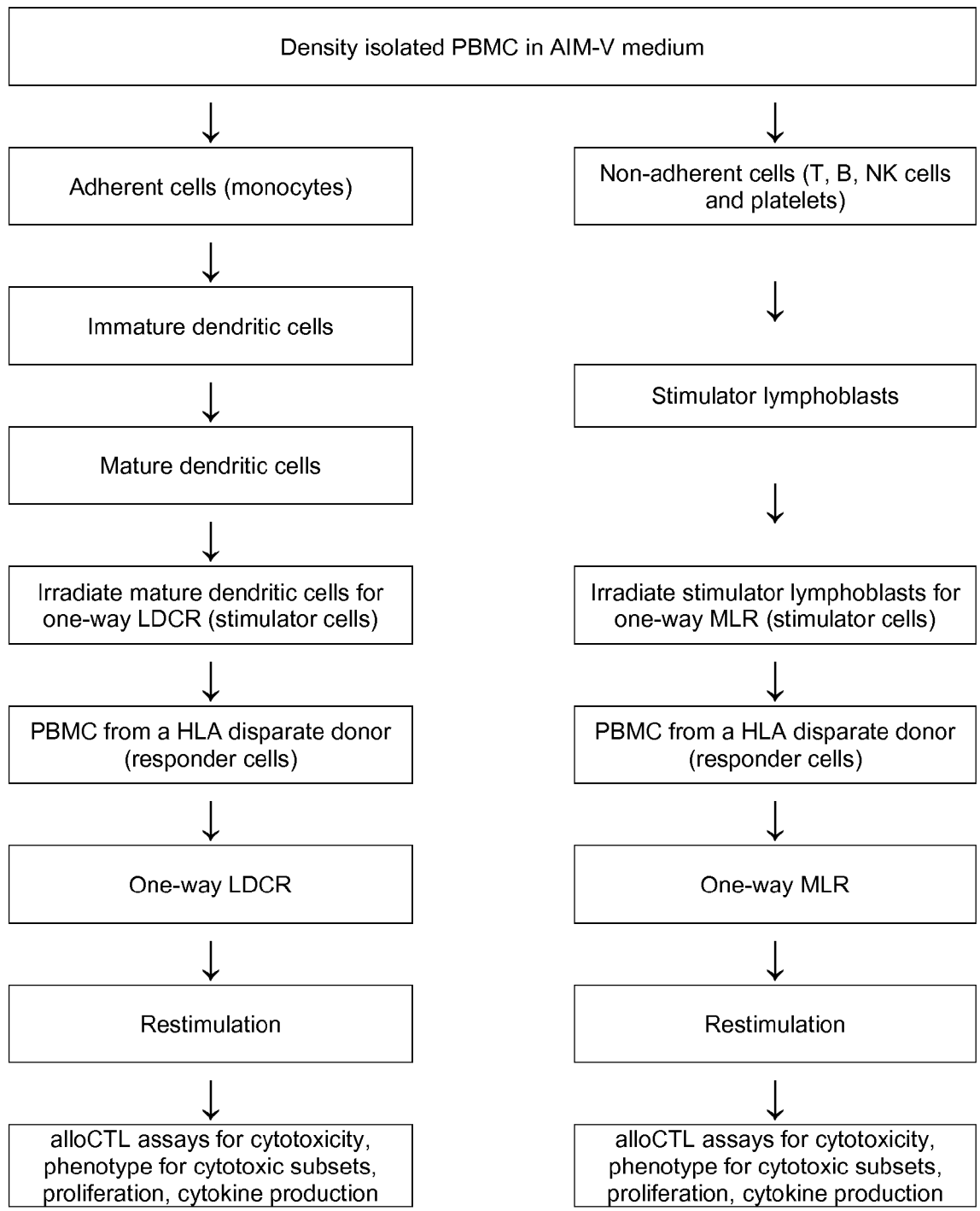

COMPOSITIONS AND METHODS OF PREPARING ALLOREACTIVE CYTOTOXIC T CELLS

CROSS-REFERENCE TO RELATED APPLICATIONS

The present application claims priority to provisional applications Ser. No. 61/229,233 filed on Jul. 28, 2009 and 61/229,229 filed on Jul. 28, 2009, the entireties of which are incorporated herein by reference.

FIELD OF THE INVENTION

The invention relates to compositions and methods for preparing alloreactive cytotoxic T cells. In one aspect of the invention, alloreactive cytotoxic T cells are generated by activating donor cells by patient stimulator cells.

BACKGROUND OF THE INVENTION

T cells can be activated by an antigen presenting cell. An activated T cell can bind to a cell that presents an antigen to which the T cell was activated via an interaction between a T cell receptor and a major histocompatibility complex, and the activated T cell can kill the cell to which it is bound. It is possible to activate T cells from a donor against cells from a patient and generate cytotoxic T cells that kill patient cells. Such T cells are referred to as "alloreactive" T cells as they are activated from donor cells and are active against patient cells.

Alloreactive cytotoxic T cells can be prepared by isolating blood from a patient, separating white blood cells, and inactivating them. These inactivated patient cells can be mixed with white blood cells from a donor in a one-way lymphocyte reaction. In the lymphocyte reaction, T cells among the donor cell population are activated against antigens presented by cells in the patient population, and activated cytotoxic T cells are generated against the patient cells. The activated cytotoxic T cells can be collected and administered to the patient. Cells in the patient, such as cancer cells, that display antigens recognized by the cytotoxic T cells will be killed.

The methods in the prior art, while effective, have shown to produce results of varying reliability.

SUMMARY OF THE INVENTION

The present invention relates to compositions and methods of preparing alloreactive T cytotoxic cells. Methods according to the invention exhibit greater reliability over methods in the prior art and generate compositions that are highly effective in treating a subject of interest, for example, a patient having a cancer such as a glioma.

In an exemplary method according to the invention, alloreactive cytotoxic T cells are prepared by isolating monocytes from a subject and by differentiating the isolated monocytes into dendritic cells. In successive steps, the dendritic cells are matured and then inactivated, and the inactivated dendritic cells are contacted with T cells from a donor to generate the alloreactive cytotoxic T cells.

The monocytes may include adherent cells and may be isolated from peripheral blood of the subject.

In different embodiments of this exemplary method, the monocytes may be differentiated into dendritic cells by using GM-CSF, IL-4.

Also in different embodiments of this exemplary method, the dendritic cells may be matured by exposing the dendritic cells to TNFalpha, IL-6, IL-1beta, and/or one or more pathogen-associated molecular patterns (PAMPs).

Still in different embodiments of this exemplary method, the matured dendritic cells may be inactivated with irradiation or with mitomycin C.

In yet different embodiments of this exemplary method, the inactivated dendritic cells may be contacted with the T cells from the donor in different ratios of donor cells to subject cells, preferably in ratios ranging from about 1:1 to about 10:1. The donor and the subject should be human leukocyte antigen (HLA) disparate, and, preferably, the patient and the donor are partially HLA disparate.

This exemplary method may further include the steps of administering the alloreactive cytotoxic T cells to the subject of interest. For example, the alloreactive cytotoxic T cells may be employed to treat a patient having cancer such a glioma in the brain. In one embodiment of the invention, the alloreactive cytotoxic T cells are administered by injection or using other means that cause a direct contact of the alloreactive cytotoxic T cells with at least some of the cancerous cells. In another embodiment, the alloreactive cytotoxic T cells are administered to an immune semi-privileged site of a patient.

An exemplary composition according to the invention includes alloreactive cytotoxic T cells from a donor, which have been activated to recognize a predetermined cell type in a subject of interest, for example, a cancerous cell in a patient. Preferably, the alloreactive cytotoxic T cells are derived from a donor that is HLA disparate with the patient, most preferably partially HLA disparate, and have been activated to recognize a peptide, or, more generally, one or more peptides derived from the HLA of the patient.

The cytotoxic T cells in this exemplary composition may have been derived from monocytes of the patient and may have been contacted with matured dendritic cells from the patient. In one embodiment of the invention, the dendritic cells have been activated during maturation by exposure to cytokines with or without one or more PAMP molecules.

This exemplary composition may also include inactivated dendritic cells that have been derived from the patient.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIG. 1 shows a bifurcated protocol for the production of alloreactive cytotoxic T cells.

DETAILED DESCRIPTION OF EMBDIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Brain tumor cells, such as glioma cells, express human leukocyte (HLA) antigens, which are generally not expressed on normal, mitotically quiescent neuroglia. Accordingly, the HLA expressed by the glioma cells can act as therapeutically useful tumor directed antigens.

Alloreactive cytotoxic T lymphocytes (alloCTL) are activated T cells that respond to peptide(s) derived from the allogeneic HLA. An immune response to major alloantigen often is stronger than an immune response engendered to minor tumor associated antigens (TAA). Furthermore, CTL precursor frequencies generally are higher to major alloantigens than to TAA. Preclinical and clinical data indicate that alloCTL adoptively transferred into the brain can induce selective destruction of glioma cells. The lack of expression of HLA antigens on normal brain tissue cells may limit the immune reaction only to tumor cells, and the relative immune privilege of the brain may extend the useful life-span of therapeutic alloCTL.

Malignant gliomas are a uniformly fatal disease. The length of survival is generally inversely related to the pathologic grade of the tumor at diagnosis. The tumors are usually resistant to conventional radiotherapy and/or chemotherapy modalities. A variety of promising immune-based protocols in Phase I testing have primarily targeted the WHO grade IV glioblastoma multiforme (GBM) patient population. Given the grave prognosis, the FDA has set precedence to allow certain experimental treatments to be given upfront rather than at recurrence.

Few protocols are available specifically for recurrent lower grade gliomas, such as anaplastic astrocytomas (AA). After conventional radiotherapy, and in suitable cases treatment with chemotherapy, median survival times are 2-3 year for patients with AA, 3-5 yr for anaplastic oligodendroglioma (AODG), and 12-15 months for GBM. Reoperation for patients with recurrent grade III AA, without other adjuvant therapy, prolonged median survival an additional 5-10 months. Reoperation may be indicated in recurrent GBM patients with mass effect, but alone will have limited value in prolonging survival. Some neuro-oncologists believe that the biology and outcomes of secondary GBMs are different than primary GBMs.

Invasive glioma cells are the origin of tumor recurrence after surgery and radiation in nearly 100% of patients. Therefore, a successful therapeutic regimen must not only eradicate the bulk of the tumor, but it must also eliminate these small pockets of infiltrating cells that diffuse away from the main tumor mass. Immune cells are normally circulating cells that can move through tissue, can kill tumor cells upon contact, and can produce cytokines that induce apoptosis or initiate an endogenous immune response.

Accordingly, alloreactive cytotoxic T cells prepared by the methods and compositions herein can be useful for treating glioma and other proliferative disorders upon administration to a patient.

Stimulator Cell and Donor Cell Preparation

After identifying the presence of a partial mismatch for a donor/patient pair, cytotoxic T cells may be prepared by mixing cells of the donor with inactivated cells of the patient for donor/patient pairs exhibiting a partial mismatch in HLA. Stimulator cells and responder cells are prepared before such an activation reaction is conducted.

Stimulator cells, which are derived from a patient, and responder cells, which are derived from a donor, independently can be from any suitable source. A source of cells includes, without limitation, blood, blood fraction (e.g., plasma, serum, buffy coat, red blood cell layer), bone marrow, biological fluid (e.g., urine, blood, saliva, amniotic fluid, exudate from a region of infection or inflammation, saliva, cerebral spinal fluid, synovial fluid), or organ, tissue, cell, cell pellet, cell extract or biopsy (e.g., brain, neck, spine, throat, heart, lung, breast, kidney, liver, intestine, colon, pancreas, bladder, cervix, testes, skin and the like). The source can be direct removal from the patient or donor, and sometimes is frozen, and at times is provided as a cell suspension. A source of cells includes, without limitation, a human or an animal (e.g., canine, feline, ungulate (e.g., equine, bovine, caprine, ovine, porcine, buffalo, camel and the like), rodent (e.g., murine, mouse, rat), avian, amphibian, reptile, fish).

Cells from a patient sometimes are from patient blood, and in certain embodiments are white blood cells or lymphocytes from the blood. Cells from a donor sometimes are from donor blood, and in certain embodiments are white blood cells or lymphocytes from the blood. Donor blood sometimes is from a blood bank. Blood sometimes is peripheral blood, sometimes is a blood fraction (e.g., buffy coat), sometimes is zero to seven days old, and at times is frozen blood or frozen blood fraction (e.g., blood cells are vitally cryopreserved).

A patient from whom stimulator cells are derived often is afflicted with a medical condition. A medical condition can be a cell proliferation condition, an autoimmune condition and/or inflammation condition (non-limiting examples are provided herein).

Donor cells or patient cells, or stimulator cells or responder cells, sometimes include an enriched fraction of a particular type of cell. The term "enriched fraction" as used in the foregoing sentence refers to 25% or more than higher of normal physiologic numbers of cells in a container (e.g., flask, tube, plate; and may be as high as 95% or more). Particular cell types include, without limitation, white blood cell, granulocyte, agranulocyte, monocyte, lymphocyte, B cell, T cell, CD4+ T cell, CD8+ T cell, natural killer cell, stem cell (e.g., CD34+ cell), lymphoblast, antigen presenting cell, dendritic cell, macrophage, neutrophil, eosinophil, basophil. An antigen presenting cell sometimes is a professional antigen presenting cell, which can include, without limitation, a dendritic cell, macrophage, B cell and activated epithelial cell.

Donor cells and/or patient cells sometimes are subjected to a treatment process before combining for activation of T cells into cytotoxic T cells. A treatment process can increase the relative amount of a particular cell type in a composition, or can generate a new cell type in a population. For example, a treatment process may be utilized to differentiate patient cells into dendritic cells or activate patient cells into lymphoblasts. Certain treatments of donor cells into stimulator cells can improve the immunogenic action of responder cells when the stimulator cells are combined with the responder cells.

However, donor cells and/or patient cells may not be subjected to a treatment process prior to combining them with one another for production of cytotoxic T cells (e.g., by mixing white blood cells from the donor with stimulator cells). In the latter embodiments, the donor cells and patient cells are responder cells and stimulator cells, respectively.

In certain treatment methods, white blood cells from a patient or donor are provided and certain cell types are separated. White blood cells sometimes are collected by isolating peripheral blood mononuclear cells (PBMC) by a suitable method (e.g., density gradient centrifugation, such as on Ficoll or Percoll gradients). In some embodiments, monocytes are separated (e.g., for differentiation into dendritic cells), and sometimes are separated by collecting cells that adhere to a solid support in a particular medium (e.g., AIM-V medium). Lymphocytes are separated (e.g., for activation of lymphoblasts) in some embodiments, and sometimes are separated by collecting cells that do not adhere to a solid support in a particular medium (e.g., commercially available AIM-V medium).

An exemplary treatment method according to the principles of the invention involves the preparation of dendritic cells (DCs). Dendritic cells can be prepared by any suitable method known in the art, and non-limiting examples of DC differentiation methods are described herein (see, e.g., Examples section). In some embodiments, DCs are separated from other cells in a population and then expanded. In such methods, DCs may be contacted with one or more antibodies that bind to DC cell markers, and the DCs may be separated by flow cytometry.

DCs may also be differentiated from precursor cells. In some DC differentiation methods, monocytes from PBMC are differentiated into immature DCs and then to mature DCs. Immature DCs sometimes are differentiated from monocytes by contacting the monocytes with one or more suitable stimulants. Any suitable medium can be utilized for differentiation of dendritic cells, for example, an AIM-V or RPMI 1640 medium. In certain embodiments, DCs are differentiated from stem cells. DCs derived from a patient and selected for combination with donor cells are of any suitable maturation or activation state and can express Toll-like receptors of various types. In certain embodiments, cultures having mature DCs are selected for combination with donor cells.

Examples of stimulants include, without limitation, cytokines, which include, for example, interleukins (e.g., IL-1-IL-18 and the like), interferons (e.g., IFN-beta, IFN-gamma and the like), tumor necrosis factors (e.g., TNF-alpha, TNF-beta and the like), lymphokines, monokines and chemokines; growth factors (e.g., transforming growth factors (e.g., TGF-alpha, TGF-beta and the like); colony-stimulating factors (e.g., granulocyte macrophage colony-simulating factor (GM-CSF), granulocyte colony-simulating factor (G-CSF) etc.); and the like.

Other stimulants include pattern recognition receptors (PRRs), which are proteins expressed by cells of the innate immune system to identify pathogen-associated molecular patterns (PAMPs) that are associated with microbial pathogens or cellular stress (such as heat shock proteins). Examples of PRRs include, without limitation, such molecules as toll-like receptors (TLRs) which include members TLR-3, TLR-7, TLR-8, and TLR-9. Examples of PAMPs include, without limitation, such molecules such as TLR-agonists, imiquimod, Monophosphoryl lipid A (MPL), fibroblast-stimulating lipopeptide-1 (FSL-1), Pam3CSK4, lipolysaccharide (aka LPS or endotoxin), peptidoglycan (cell walls), lipoproteins (bacterial capsules), hypomethylated DNA (such as CpG found in bacteria and other parasites), double-stranded DNA as found in viruses, and flagellin (bacterial flagella).

In some embodiments, monocytes are contacted with one or more interleukins (e.g., IL-4), and/or one or more colony-stimulating factors (e.g., GM-CSF). In certain embodiments, monocytes and/or immature DCs are contacted with one or more interleukins (e.g., IL-6, IL-1beta) and/or one or more tumor necrosis factors (e.g., TNF alpha). A suitable amount of stimulant is selected as known in the art, and the amount of a stimulant can range from about 5 units to about 5000 units (e.g., International Units). In some embodiments, about 0.2 ng/ml to about 1000 ng/ml of a stimulant is utilized. A stimulant can be native polypeptide purified from a cell and often is recombinant polypeptide. A stimulant often is a human polypeptide, and often is produced by recombinant methods (e.g., recombinant human IL-2 (rhIL-2)).

A DC can be differentiated from a stem cell in some embodiments. In certain non-limiting DC differentiation methods, a hematopoietic stem cell (e.g., a human CD34+ stem cell) can be differentiated into a dendritic cell. Stem cells can be isolated by methods known in the art. For example, bone marrow aspirations from iliac crests can be performed e.g., under general anesthesia in the operating room. The bone marrow aspiration sometimes is approximately 1,000 ml in quantity and often is collected from the posterior iliac bones and crests. If the total number of cells collected is less than about $2 \times 10^8$/kg, a second aspiration is optionally performed (e.g., using the sternum and/or anterior iliac crests in addition to posterior crests). During the operation, two units of irradiated packed red cells can be administered to replace the volume of marrow taken by the aspiration. Human hematopoietic progenitor cells and stem cells can be characterized by the presence of a CD34 surface membrane antigen. This antigen often is used for purification.

After the bone marrow is harvested, the mononuclear cells can be separated from other components by density gradient centrifugation. This centrifugation can be performed by a semi-automated method using a cell separator (e.g., a Baxter Fenwal CS3000+ or Terumo machine). The light density cells, composed mostly of mononuclear cells, are collected and the cells are incubated in plastic flasks at 37° C. for 1.5 hours. The adherent cells (e.g., monocytes, macrophages and B-Cells) often are discarded. The non-adherent cells can be collected can be incubated with a monoclonal anti-CD34 antibody (e.g., the murine antibody 9C5) at 4° C. for 30 minutes with gentle rotation. The final concentration for the anti-CD34 antibody often is 10 micrograms/ml.

After two washes, paramagnetic microspheres (Dyna Beads, supplied by Baxter Immunotherapy Group, Santa Ana, Calif.) coated with sheep antimouse IgG (Fc) antibody can be added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml can be added to release the beads from the CD34+ cells. Alternatively, an affinity column isolation procedure can be used which binds to CD34, or to antibodies bound to CD34.

Stem cells can be differentiated in vitro using appropriate cytokines (e.g., GM-CSF). The concentration of GM-CSF in culture can be about 0.2 ng/ml or more, sometimes about 1 ng/ml or more, and at times between about 20 ng/ml and about 200 ng/ml (e.g., about 100 ng/ml), in certain embodiments. In some embodiments, TNF-alpha also is added to facilitate differentiation, sometimes in about the same concentration range as for GM-CSF. Optionally, a proliferation ligand (e.g., stem cell factor (SCF), Flt 3 ligand) is added in similar concentration ranges to differentiate human DCs, and in some embodiments, IL-4 is added in similar ranges to promote DC differentiation. In certain embodiments, a DC or DC precursor cell is transduced with a nucleic acid. The nucleic acid may encode an interleukin and/or a colony-stimulating factor (e.g., IL-4 and/or GM-CSF; U.S. Pat. No. 7,378,277, Hwu et al.). A transduction-facilitating agent (e.g., lipofectamine) can be introduced to facilitate nucleic acid transfer to cultured cells. Optimized concentrations of stimulants described in this paragraph can be assessed by titrating stimulant and observing effects (e.g., U.S. Pat. No. 7,378,277, supra).

In certain non-limiting DC differentiation methods, peripheral blood mononuclear cells (PBMCs) from healthy donors can be isolated by density centrifugation of heparinized blood on Lymphoprep (Nycomed, Oslo, Norway). PBMCs can be washed with PBS, resuspended in CellGenix DC medium (Freiburg, Germany) and allowed to adhere in culture plates for 2 h at 37° C. and 5% CO2. Nonadherent cells can be removed by extensive washings, and adherent monocytes can be cultured for 5 days in the presence of 500 U/ml hIL-4 and 800 U/ml hGM-CSF (R&D Systems, Minneapolis, Minn.). As assessed by morphology and FACS analysis, resulting immature DCs (imDCs) often are MHC-class I, IIhi, and often express CD40lo, CD80lo, CD83lo, and/or CD86lo. Immature DCs often are CD14 neg and contain less than 3% of contaminating CD3+ T, CD19+ B, and CD16+ NK cells. DCs can be stimulated with monophosphoryl lipid A (MPL), fibroblast-stimulating lipopeptide-1 (FSL-1), Pam3CSK4 (InvivoGen, San Diego, Calif.), lipopolysaccharide (LPS) (Sigma-Aldrich, St. Loucan be, Mo.), AP20187 (ARIAD Pharmaceuticals, Cambridge, Mass.) or maturation cocktail (MC), containing 10 ng/ml TNF-alpha, 10 ng/ml IL-1beta, 150 ng/ml IL-6 (R&D Systems, Minneapolis, Minn.) and 1 micrograms/ml of PGE2 (Cayman Chemicals, Ann Arbor, Mich.). Other methods for differentiating DCs from PBMC of a patient are described herein (e.g., Examples section).

Lymphoblasts also may be prepared as stimulator cells by activating patient lymphocytes, in certain embodiments. Any suitable method may be used to treat lymphocytes and activate lymphoblasts, and an example is provided herein (e.g., Examples section). Lymphoblasts can be activated from lymphocytes by contacting the latter with one or more suitable stimulants.

In certain embodiments, patient lymphocytes are contacted with one or more suitable interleukins (e.g., IL-2). An amount of an interleukin often is selected for specific expansion of sensitized cells, as known in the art (e.g., 60 International Units of recombinant human IL-2 can be utilized). Lymphocytes also can be contacted with an agent that interacts with T cells (e.g., binds to a T cell receptor), such as an antibody for example (e.g., OKT3 murine monoclonal IgG2a antibody that binds to CD3 T cell receptor complex). Any suitable medium can be utilized for activation of lymphoblasts (e.g., AIM-V medium).

Methods are known in the art for isolating and expanding T cells. In certain non-limiting T cell isolation and expansion methods, Ficoll-Hypaque density gradient centrifugation can be used to separate PBMC from red blood cells and neutrophils according to established procedures. Cells can be washed with modified AIM-V (i.e., AIM-V (Invitrogen Corporation) supplemented with 2 mM glutamine, 10 micrograms/ml gentamicin sulfate, 50 micrograms/ml streptomycin supplemented with 1% fetal bovine serum (FBS). Enrichment for T cells can be performed by negative or positive selection with appropriate monoclonal antibodies coupled to columns or magnetic beads according to standard techniques. An aliquot of cells can be analyzed for cell surface phenotype including CD4, CD8, CD3 and CD14.

Cells can be washed and resuspended at a concentration of $5 \times 10^5$ cells per ml of AIM-V modified as above and containing 5% FBS and 100 U/ml recombinant IL-2 (rIL-2) (in supplemented AIM-V). Where cells are isolated from a HIV+ patient, 25 nM CD4-PE40 (a recombinant protein consisting of the HIV-1-binding CD4 domain linked to the translocation and ADP-ribosylation domains of *Pseudomonas aeruginosa* exotoxin A), or other similar recombinant cytotoxic molecule which selectively hybridizes to HIV, can be added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells. To stimulate proliferation, OKT3 monoclonal antibody (Ortho Diagnostics) can be added at a concentration of about 10 ng/ml and the cells can be plated in 24 well plates with 0.5 ml per well. The cells can be cultured at 37° C. in a humidified incubator with 5% $CO_2$ for 48 hours.

In some embodiments, stimulator cells are subjected to a process that yields inactivated stimulator cells. Inactivated stimulator cells often are not capable of dividing, and often are not capable of certain functions (e.g., killing other cells). Inactivated stimulator cells are capable of activating T cells present in the responder cell population against patient antigens. Inactivated stimulator cells often retain cell surface structure, and generally are capable of presenting antigen to responder cells (e.g., presentation of antigen by way of MHC to T cell receptor of a responder cell). Methods for inactivating stimulator cells are known in the art, which include, without limitation, irradiating stimulator cells or contacting stimulator cells with mitomycin C.

Combining Stimulator Cells and Responder Cells

Stimulator cells, from a patient or derived from patient cells, and responder cells, from a donor or derived from donor cells, may be combined with one another to generate activated cytotoxic T cells. Such activated cytotoxic T cells generally arise from the responder cell population, and often are "alloreactive," meaning that they are active against the stimulator cells. Without being bound by theory, responder cells include T cells that are activated by antigens presented by stimulator cells, and the resulting activated cytotoxic T cells are capable of killing the stimulator cells, and cells of the patient. In certain embodiments, stimulator cells include (i) inactivated dendritic cells differentiated from patient cell monocytes, (ii) inactivated lymphoblasts activated from patient cell lymphocytes, and/or (iii) inactivated patient cell white blood cells (e.g., PBMC). In some embodiments, responder cells are lymphocytes from a donor. Combining stimulator cells and responder cells with the expectation of generating alloreactive cytotoxic T cells sometimes is referred to herein as an "activation reaction."

Certain donors are selected as sources of responder cells for generation of cytotoxic T cells in an activation reaction. In some embodiments, a donor is selected who is unrelated by family relationship to the patient.

In certain embodiments, a donor is selected based on having a partial antigen mismatch with a patient. A partial mismatch generally is not a full match and often is at a less restrictive degree of matching than for an organ donor-patient pairing. A partial mismatch generally is a greater degree of matching than a total mismatch. An "antigen unit" as used herein refers to antigen information that can be assessed by a method known in the art (e.g., HLA group allele; measure of T cell receptor/MHC peptide interaction. An example of a mismatch at the serologic level would be HLA A1 vs A2. An example of a mismatch at the molecular level would be if responder and donor are A2, the difference might be at the aa level such as A*0201 or A*0202. Where antigen units are compared, a partial mismatch sometimes is 1, 2, 3, 4, 5 or 6 patient/donor antigen units mismatched short of a full match in some embodiments, and in certain embodiments, a partial mismatch sometimes is 1, 2, 3, 4, 5 or 6 patient/donor antigen units matched short of a full mismatch. A partial mismatch may be identified when there are one or more amino acid mismatches between counterpart HLA molecules of a donor and patient.

Patient antigen information and donor antigen information can be any suitable antigen information useful for determining antigen discrepancy for the preparation of cytotoxic T cells. In certain embodiments, major histocompatibility complex (MHC) information, which also is referred to as human leukocyte antigen (HLA) information, is provided. HLAs are encoded by the HLA loci on human chromosome 6p. HLA information includes, without limitation, HLA class I information, HLA class II information, a combination of both, and any other suitable antigen information.

HLA class I molecules often present peptides from about 1 to 9 amino acids in length, and HLA class II molecules often present peptides from about 1 to 15-24 amino acids in length. HLA class I molecules often present peptides from within the cell, and HLA class II molecules often present peptides from a source outside the cell that is brought into the cell for presentation. An HLA molecule can interact with a CD8+ activated T cell that recognizes the peptide presented by the HLA molecule, and the T cell can kill the cell bearing the HLA molecule with which the T cell interacts.

There are different groups of HLA class I molecules that include, without limitation, HLA-A-A-HLA-L groups. Each group of HLA class I molecules includes multiple alleles. For example, HLA-A*0101, *0102, *0103, . . . *0130 are assigned to the serotype A1. The "A*01" prefix signifies that the gene products (expressed proteins) of the alleles are primarily identified by the A1 serotype or most similar to alleles recognized by the serotype. There are different groups of HLA class II molecules that include, without limitation, HLA-DM, HLA-DQ, HLA-DP, HLA-DO and HLA-DR groups. Each group of class II molecules encodes alpha-beta heterodimer proteins, and includes multiple alleles. For example, the HLA-DR group of HLA class II molecules includes DRB1*0101, DRB1*0102, DRB1*0103 and other alleles. For mammalian patients and donors (e.g., humans), each patient and donor cell bears two alleles (fraternal and paternally derived) in each group. Thus, patient and donor cells each have two HLA-A alleles, two HLA-B alleles and so on.

Patient and donor antigen information sometimes are referred to herein as "antigen units," and each antigen unit sometimes is an allele. Antigen information is one or more alleles in certain embodiments, and in some embodiments is between about 2 to about 38 alleles. Antigen information sometimes includes one allele for each HLA group provided, or both alleles of each HLA group provided. In some embodiments, antigen information includes one or two alleles from HLA groups (e.g., about 1 to about 19 HLA groups).

Methods for determining an HLA allele are known in the art. For example, an HLA allele can be determined by methods that include, but are not limited to, molecular typing, haplotyping, gene sequencing, cellular typing and serotyping. In molecular typing methods, for example, an amplification reaction (e.g., polymerase chain reaction (PCR)), can be utilized with sequence specific primers (SSPs), where the size of an amplification product, and/or a sequence in or of an amplification product, can be assessed to determine an HLA type (e.g., HLA allele). The latter method sometimes is referred to as SSP-PCR when PCR is utilized as the amplification process.

A molecular typing method, in some embodiments, can involve identification of a sequence in or of a product of an amplification reaction (e.g., sequence base typing (SBT)). In SBT an amplification product sometimes is immobilized and contacted with sequence specific primers to determine a sequence of the product. Molecular typing also can be accomplished in some embodiments by a restriction fragment length polymorphism (RFLP) method in which one or more amplification products are digested with one or more enzymes, and the resulting fragments are analyzed. In molecular typing methods that utilize an amplification reaction, nested amplification reactions can be utilized in some embodiments. Haplotyping often involves determining multiple HLAs on one nucleic acid strand of a subject.

Gene sequencing methods generally involve sequencing all or a part of an HLA from a patient or donor using known sequencing methodology (e.g., SBT-PCR). Serotyping often involves reacting cells from a patient or donor with blood, antiserum and/or an antibody and determining which HLA antigens are present in the cell. In serotyping procedures, a cross-reacting HLA antigen can be recognized by monospecific antibodies (e.g., monoclonal or polyclonal) in certain embodiments. A cellular typing method, such as a mixed lymphocyte culture (MLC) method, can be used to determine presence of an HLA allele by selective activation of a particular T cell type. In some embodiments, a molecular typing method (e.g., SSP-PCR, SBT and/or RFLP method) is utilized to generate antigen information for a donor and/or patient, and in certain embodiments, antigen information from a donor and/or a patient is obtained, or is complemented, with a cellular typing and/or cellular typing method.

Stimulator cells and responder cells can be combined in any suitable ratio for generating activated cytotoxic T cells. In certain embodiments, the ratio of stimulator:responder cells is about 1:10, and but different ratios may be employed in other embodiments, for example, 1:2, −1:20. The stimulator cells and responder cells are combined under conditions conducive to generating activated cytotoxic T cells. Such conditions can include one or more stimulants (e.g., low dose IL-2 (60 IU/ml for DC stimulator cells)). Culture conditions can include a suitable medium (e.g., AIM-V medium) with or without serum (e.g., 5% autologous serum). In embodiments where serum is utilized in culture medium, cells may be weaned from serum-containing medium over time. Stimulator cells and responder cells may be combined for any suitable period of time, including, without limitation, 2-25 or more days. Responder cells may be re-stimulated one or more times (e.g., 1-10 or more times) with additional stimulator cells, which can be combined at a stimulator:responder cell ratio described above. Re-stimulation can be for any suitable period of time, such as a period of time described above for the initial stimulation.

Alloreactive cytotoxic T cells resulting from the combination of stimulator cells and responder cells can be identified, separated and/or purified by methods described herein. Cytotoxic T cells also may be administered to a patient, with or without identification, separation or purification, to treat a condition or disorder, as addressed in more detail hereafter.

Characterization of Cells and Activities

Methods for assessing stimulator cells, responder cells and activated cytotoxic T cells are known in the art. Such methods can be carried out at a suitable time point, and some are performed before patient cells are exposed to activation or differentiation conditions, before stimulator cells and responder cells are combined and/or after the latter cells are combined. For example, certain methods assess the ability of antigen presenting cells (e.g., patient cells, DCs, lymphoblasts) to activate responder cells (e.g., donor cells, T cells), and some methods assess the activity of activated responder cells (e.g., donor cells, T cells). Examples of such methods are described herein (e.g., Examples section).

Presence, absence or amount of cell surface markers and/or production of certain cytokines can be utilized to determine whether certain cells have reached a particular maturation or activation state (e.g., mature dendritic cell, activated T cell). Levels of a stimulant in the cytoplasm of cells, or secreted by cells, also can be assessed. For example, activated T cells produce interferon (IFN) gamma, which can be assayed as described herein (e.g., using an antibody that binds IFN-gamma; Examples section). Cytokines can be measured in culture supernatants using commercially available enzyme-linked immunosorbent assay kits (e.g., human IL-6 and IL-12p70 (BD Biosciences)).

A cell having a certain feature (e.g., one or more cell surface markers) can be identified, separated and/or purified from cells not having that feature. Presence, absence of amount of a surface marker facilitates identification, separation and/or purification of immunologic cells known in the art. For example, cells in a population can be contacted with an antibody that binds to a particular cell marker on a subset of the cells. Cells that display the marker and bind the antibody can be separated from cells that do not display the marker and do not bind the antibody. A fluorescence activated cell sorter (FACS) can be utilized to separate certain cell types from others, and the separated cells can be assessed and/or further manipulated.

Cell surface markers expressed, or not expressed, on the cell surface at a particular state of differentiation or activation are known. For example, markers are available to identify activated cytotoxic T cells (e.g., CD8+, CD3+, CD69+); immature T cells (e.g., CD4− and CD8−); helper T cells (e.g., CD3+, CD4+ and CD8+); regulatory T cells (e.g., CD4+/CD25+ or Foxp3+ and production of certain cytokines (e.g., IL-10 and/or TGF-beta)); NK cells (CD3−, CD16+), human stem cells (e.g., CD34+, CD15+). DCs express MHC molecules (e.g., HLA class I molecules, HLA class II molecules), co-stimulatory molecules (e.g., CD80+ (B7.1), CD86+ (B7.2), and CD40+, which are co-receptors in T-cell activation that enhance the DC's ability to activate T-cells) and chemotactic receptor (e.g., CCR7+). Other markers that can be detected on DCs include, without limitation, CD11c, CD83 and CD86. DCs lack markers specific for granulocytes, NK cells, B cells, and T cells. In some instances, DCs express 33D1 (DC from spleen and Peyer's patch, but not skin or thymic medulla), NLDC145 (DC in skin and T-dependent regions of several lymphoid organs and CD11c (CD11c also reacts with macrophage)). Agents that bind to markers are known in the art and are commercially available (e.g., antibodies bound to a detectable label) and methods for identifying, separating and purifying cells using such agents are known (e.g., described herein). Cell surface staining can be performed using fluorochrome-conjugated monoclonal antibodies (BD Biosciences, San Diego, Calif.). Cells can also be phenotypically analyzed using a flow cytometer (e.g., FACSCalibur or LSR II cytometer (BD Biosciences, San Jose, Calif.)).

Cells can be identified, separated and/or purified before being treated (e.g., differentiation into DCs or activation into lymphoblasts), after being treated, after exposure to a condition that generates inactivated cells, after being combined with a stimulator or responder counterpart, or after administration to a patient. For example, separated cells may be exposed to conditions that produce differentiated cells (e.g., DCs), activated cells (e.g., lymphoblasts, activated T cells) and/or inactivated cells (e.g., inactivated DCs, inactivated lymphoblasts), in some embodiments. Separated cells also may be administered to a subject for cell therapy (e.g., activated T cells may be administered), in certain embodiments. Separated cells can be substantially free from other cell types (e.g., substantially isolated). A cell having a particular marker, or a particular cell type, maybe enriched or represent about 60% or more of the cells in a population of cells, up to 95% or more in a population of cells).

Depending upon the assay or separation technique utilized, various components, including an antibody, sometimes are bound to a solid surface. For instance, in certain embodiments, unwanted cells are panned out of bone marrow using appropriate antibodies bound to a substrate over which cells are passed. Methods for immobilizing biomolecules to a variety of solid surfaces are known in the art. For instance, a solid surface sometimes is a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, a flask, or a glass, silica, plastic, metallic or polymer bead. The desired component sometimes is covalently bound, or non-covalently attached (e.g., through nonspecific bonding) in certain embodiments. Organic and inorganic polymers, natural and synthetic, are known and sometimes employed as a solid surface material. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials sometimes include paper, glasses, ceramics, metals, metalloids, semiconductive materials, cements and the like. Substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts also can be selected and utilized.

Certain assays can detect cell proliferation. In certain embodiments, T cells in a responder cell population proliferate in response to stimulator cells, and progress or success (or lack thereof) of an activation reaction can be assessed. In certain non-limiting examples of a cell proliferation assay, cells can be pulsed with a radiolabeled nucleotide (e.g., tritiated thymidine), and the amount of radiolabeled nucleotide incorporated into cellular DNA can be assessed (e.g., the higher amount of incorporation the high level of proliferation). An example of such an assay is described herein (e.g., Examples section).

In some embodiments, certain assays detect one or more ratios of stimulators (e.g., cytokines) produced during activation reactions. Such ratios can be indicative of the progress or success (or lack thereof) of an activation reaction. In some assay embodiments, a T helper 1 (Th1) to T helper 2 (Th2) cytokine ratio is assessed. A ratio of suitable stimulators can be assessed, and in some embodiments, a ratio between any two of the following stimulators can be determined: IFN-gamma, TNF-alpha, IL-2, IL-4, IL-5 and IL-10. In certain embodiments, a ratio is determined for (i) IFN-gamma to IL-10, and/or (ii) TNF-alpha to IL-4.

Certain assays can assess cytotoxic T cell activity by detecting one or more cytokines generated by activated T cells (e.g., granulocyte-macrophage colony-stimulating factor (GM-CSF), interferon (IFN) gamma, tumor necrosis factor (TNF) alpha). In a non-limiting example of an IFN-gamma assay, DCs from HLA-A2-positive healthy volunteers can be pulsed with MAGE-3 A2.1 peptide (residues 271-279; FLWGPRALV) on day 4 of culture, followed by transduction with Ad-iCD40 and stimulation with various stimuli on day 5. Autologous T cells can be purified from PBMCs by negative selection (Miltenyi Biotec, Auburn, Calif.) and mixed with DCs at DC:T cell ratio 1:3. Cells can be incubated in complete RPMI with 20 U/ml hIL-2 (R&D Systems) and 25 micrograms/ml of MAGE 3 A2.1 peptide. T cells can be restimulated at day 7 and assayed at day 14 of culture. For quantification, flat-bottom, 96-well nitrocellulose plates (MultiScreen-HA; Millipore, Bedford, Mass.) can be coated with IFN-gamma mAb (2 µg/ml, 1-D1K; Mabtech, Stockholm, Sweden) and incubated overnight at 4° C. After washings with PBS containing 0.05% TWEEN 20, plates can be blocked with complete RPMI for 2 h at 37° C. A total of $1\times10^5$ presensitized CD8+ T effector cells can be added to each well and incubated for 20 h with 25 micrograms/ml peptides. Plates then can be washed thoroughly with PBS containing 0.05% Tween 20, and anti-IFN-mAb (0.2 μg/ml, 7-B6-1-biotin; Mabtech) can be added to each well. After incubation for 2 h at 37° C., plates can be washed and developed with streptavidin-alkaline phosphatase (1 μg/ml; Mabtech) for 1 h at room temperature. After washing, substrate (3-amino-9-ethyl-carbazole; Sigma-Aldrich) can be added and incubated for 5 min. Plate membranes displaying dark-pink spots that can be scanned and analyzed by ZellNet Consulting Inc. (Fort Lee, N.J.).

Certain assays for cytotoxic T cell activity can assess the cell-killing (e.g., cell lysis) activity of activated T cells. Certain assays detect a component inside a cell released when it is killed by an activated T cell, and one example is a chromium release assay. In a non-limiting example of a chromium release assay, antigen recognition can be assessed using target cells labeled with 51Chromium (Amersham) for 1 h at 37° C. and washed three times. Labeled target cells (5000 cells in 50 μl) can be then added to effector cells (100 μl) at certain effector:target cell ratios in V-bottom microwell plates at certain concentrations. Supernatants can be harvested after 6-h incubation at 37° C., and chromium release is measured using MicroBeta Trilux counter (Perkin-Elmer Inc, Torrance Calif.). Assays involving LNCaP cells can be run for 18 hours. The percentage of specific lysis is calculated as: 100* [(experimental−spontaneous release)/(maximum−spontaneous release)].

Specificity of activated T cells also can be assessed by methods known in the art. For example, a tetramer staining assay which identifies TAA can be utilized to determine activated T cell specificity. In a non-limiting example of a tetramer staining assay, HLA-A2 tetramers assembled with MAGE-3.A2 peptide (FLWGPRALV) can be obtained from Baylor College of Medicine Tetramer Core Facility (Houston, Tex.). Presensitized CD8+ T cells in 50 μl of PBS containing 0.5% FCS can be stained with PE-labeled tetramer for 15 min on ice before addition of FITC-CD8 mAb (BD Biosciences). After washing, results can be analyzed by flow cytometry. The assay described in this paragraph utilizes a particular peptide (i.e., MAGE-3.A2 peptide) that may or may not be applicable to certain therapeutic methods and compositions described herein, and another relevant peptide may be substituted.

A polarization assay can be utilized to determine whether antigen presenting cells are capable of activating T cells from a donor by assaying for activated cells that display CD4 and IFN-gamma markers. In a non-limiting example of a polarization assay, naïve CD4+ CD45RA+ T-cells from HLA-DR11.5-positive donors (genotyped using FASTYPE HLA-DNA SSP typing kit; BioSynthesis, Lewisville, Tex.) can be isolated by negative selection using naïve CD4+ T cell isolation kit (Miltenyi Biotec, Auburn, Calif.). T cells can be stimulated with autologous DCs pulsed with tetanus toxoid (5 FU/ml) and stimulated with various stimuli at a stimulator to responder ratio of 1:10. After 7 days, T cells can be restimulated with autologous DCs pulsed with the HLA-DR11.5-restricted helper peptide TTp30. Cells can be stained with PE-anti-CD4 Ab (BD Biosciences), fixed and permeabilized using BD Cytofix/Cytoperm kit (BD Biosciences), then stained with hIFN-gamma mAb (eBioscience, San Diego, Calif.) and analyzed by flow cytometry. Supernatants can be analyzed using human TH1/TH2 BD Cytometric Bead Array Flex Set on BD FACSArray Bioanalyzer (BD Biosciences). The assay described in this paragraph utilizes a particular peptide (i.e., peptide TTp30) that may or may not be applicable to certain therapeutic methods and compositions described herein, and another relevant peptide may be substituted (e.g., another HLA peptide may be utilized and donors having an HLA that presents the peptide can be selected).

Any suitable assay can be utilized to determine the activity of DCs as they are differentiated. A migration assay (e.g., chemotaxis assay) can be utilized to determine whether viable dendritic cells are present in a culture medium, for example, and methods for assessing DC migration are known in the art. In a non-limiting example, migration of DCs can be measured by passage through a polycarbonate filter with 8 micrometer pore size in 96-Multiwell HTS Fluoroblok plates (BD Biosciences). Assay medium (250 μL) containing 100 ng/ml CCL19 (R&D Systems) or assay medium alone (as a control for spontaneous migration) can be loaded into a lower chamber. DCs (50,000) can be labeled with Green-CMFDA cell tracker (Invitrogen), unstimulated or stimulated for 48 h with the indicated reagents, and can be added to an upper chamber in a total volume of 50 μL for 1 hour at 37° C. and 5% $CO_2$. Fluorescence of cells, which have migrated through the microporous membrane, can be measured using the FLU-Ostar OPTIMA reader (BMG Labtech Inc., Durham, N.C.). The mean fluorescence of spontaneously migrated cells can be subtracted from the total number of migrated cells for each condition.

Administration of Cytotoxic T Cells and Treatments

Cytotoxic T cells herein provided may be formulated in a pharmaceutical composition in any manner appropriate for administration to a subject. A composition may be prepared by washing cells one or more times with a medium compatible with cells of the subject (e.g., phosphate buffered saline). Cells also may be combined with components that form a time-release matrix or gel in some embodiments. Non-limiting examples of components that form a matrix include, without limitation, fibrin, proteoglycans or polysaccharides. A matrix sometimes is a thrombus or plasma clot in some embodiments.

Compositions comprising cytotoxic T cells can be administered to patients for treatment of a condition. The cytotoxic T cells often are administered to the same patient from whom stimulator cells were derived used to generate the T cells. In some embodiments, cytotoxic T cells are administered to a subject who is not the patient from which the stimulator cells used to prepare the T cells were derived.

A composition can be administered to a subject in need thereof in an amount effective to treat a cell proliferative condition (e.g., cancer, tumor), inflammation condition or autoimmune condition. The terms "treat" and "treating" as used herein refer to (i) preventing a disease or condition from occurring (e.g. prophylaxis); (ii) inhibiting the disease or condition or arresting its development; (iii) relieving the disease or condition; and/or (iv) ameliorating, alleviating, lessening, and removing symptoms of the disease or condition. The terms also can refer to reducing or stopping a cell proliferation rate (e.g., slowing or halting tumor growth) or reducing the number of proliferating cancer cells (e.g., removing part or all of a tumor).

Given that activated T cells often are alloreactive and can kill cells of a patient that present patient antigen to which the cytotoxic T cells are sensitized, the T cells often are administered in a manner that does not lead to significant killing of non-afflicted tissue. Activated T cells also often are administered to a part of the body that does not rapidly inactivate the administered T cells. In certain embodiments, activated T cells can be administered to an immuno-privileged region of a subject. An immuno-privileged region sometimes is characterized by one or more of the following non-limiting features: low expression of MHC molecules; increased expression of surface molecules that inhibit complement activation; local production of immunosuppressive cytokines such as TGF-beta; presence of neuropeptides; and constitutive expression of Fas ligand that controls the entry of Fas-expressing lymphoid cells. An immuno-privileged region can be semi-immuno-privileged, where a minority subset of cells are subject to the immune system. In certain embodiments, a composition is administered to the brain, an immuno-privileged region, to treat a cancer, where cancer cells are the predominant antigen presenting cells and are preferentially killed by the T cells over non-cancer cells. Other non-limiting examples of immuno-privileged regions of the body are portions of the eye (e.g., ocular anterior chamber, ocular uveal tract, cornea, central nervous system), testis, liver and pregnant uterus.

Activated T cells also may be administered to another part of the body that is not immuno-privileged, in certain embodiments. In some embodiments, activated T cells are administered to a part of the body where T cells are not substantially cleared or inactivated. For example, activated T cells may be administered directly to a solid tumor mass, where the T cells may not be readily transported to other parts of the body or inactivated (e.g., injected into the tumor). Compositions can be administered to the subject at a site of a tumor, in some embodiments. Diffuse cancers are treatable where the composition is maintained in contact with cells within a limited area (e.g., within the cranial cavity), in certain embodiments.

Cytotoxic T cells are delivered in any suitable manner. A dose can be administered by any suitable method, including, but not limited to, systemic administration, intratumoral administration, bolus injection, infusion, convection enhanced delivery, blood-brain barrier disruption, intracarotid injection, implant delivery (e.g., cytoimplant), and combinations thereof (e.g., blood-brain barrier disruption followed by intracarotid injection). Blood-brain barrier disruption can include, without limitation, osmotic disruption; use of vasoactive substances (e.g, bradykinin); exposure to high intensity focused ultrasound (HIFU); use of endogenous transport systems, including carrier-mediated transporters such as glucose and amino acid carriers, for example; receptor-mediated transcytosis for insulin or transferrin; blocking of active efflux transporters such as p-glycoprotein, for example; intracerebral implantation; convection-enhanced distribution; use of a liposome; and combinations of the foregoing. Cytotoxic T cells are delivered by injection in a suitable volume (e.g., about 5 ml to about 20 ml volume (e.g., about 10 ml volume)), and in a suitable medium (e.g., saline; phosphate buffered saline), and with or without cytokines that help maintain activation state, (i.e., IL-2, IL-12). An implant sometimes includes a gel or matrix. In certain embodiments, an infusion is via a catheter and/or reservoir (e.g., Rickham, Ommaya reservoir).

The dose given is an amount "effective" in bringing about a desired therapeutic response (e.g., destruction of cancer cells) by the alloreactive cytotoxic T cells in the composition. For pharmaceutical compositions described herein, an effective dose often falls within the range of about $10^8$ to $10^{11}$ cells. The cells can include allogeneic stimulators and responders, or may be purified to a certain degree (e.g., substantially pure) for responder cells (e.g., activated T cells). About $1 \times 10^9$ to about $5 \times 10^{10}$ cells sometimes are delivered, in some embodiments, and in certain embodiments, about $10^8$ to about $10^{10}$ cells, about $10^9$ to about $10^{11}$ cells, about $10^8$ to about $10^9$ cells, about $10^9$ to about $10^{10}$ cells, about $10^{10}$ to about $10^{11}$ cells, about $2 \times 10^9$ to about $2 \times 10^{10}$ cells, or about $2 \times 10^9$ to about $2 \times 10^{10}$ cells, are delivered. Multiple doses can be delivered over time to achieve a desired effect, and often, each dose delivers an effective amount of cells. Cells in the composition delivered can contain a mixture of responder cells and inactivated stimulator cells, sometimes in a ratio between about 1:1 and about 100:1, and sometimes in a ratio between about 5:1 and about 25:1, and sometimes about 10:1. In some embodiments, cytotoxic T cells are enriched or purified to a certain degree (e.g., cytotoxic T cells could be about 30% or more of cells in the composition, up to more than 95% of cells in the composition) and other accessory cells (NK or NKT or CE4+ T cells) may be carried along in the preparation that may have cytotoxic or helper function(s). Any number of component cells or other constituents may be used, as long as the composition is effective as a whole. The number of cells utilized in a composition also can depend on culture conditions and other factors during preparation.

A pharmaceutical composition provided herein may be administered following, preceding, in lieu of, or in combination with, one or more other therapies relating to generating an immune response or treating a condition in the subject (e.g., cancer). For example, the subject may previously or concurrently be treated by chemotherapy, radiation therapy, surgery, cell therapy and/or a form of immunotherapy and adoptive transfer. Where such modalities are used, they often are employed in a way or at a time that does not interfere with the immunogenicity of compositions described herein. The subject also may have been administered another vaccine or other composition to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

Non-limiting examples of chemotherapeutic agents include, without limitation, alkylating agents (e.g., cisplatin); antimetabolites (e.g., purine, pyrimidine); plant alkaloids and terpenoids (e.g., taxanes); vinca alkaloids and topoisomerase inhibitors. Surgeries sometimes are tumor removal or cytoreduction, the latter of which is removal of as much tumor as possible to reduce the number of tumor cells available for proliferation. Surgeries include, without limitation, surgery through the nasal cavity (trans-nasal), surgery through the skull base (trans-sphenoidal), and craniotomy (opening of the skull). Radiotherapies include, without limitation, external beam radiotherapy (EBRT or XBRT) or teletherapy, brachytherapy or sealed source radiotherapy, systemic radioisotope therapy or unsealed source radiotherapy, virtual simulation, 3-dimensional conformal radiotherapy, intensity-modulated radiotherapy, particle therapy and radioisotope therapy. Conventional external beam radiotherapy (2DXRT) often is delivered via two-dimensional beams using linear accelerator machines. Stereotactic radiotherapy is a type of external beam radiotherapy that focuses high doses of radiation within the body (e.g., cyberknife, gamma knife and Novalis Tx). Cell therapies include, without limitation, administration alone or in combination of dendritic cells, alloreactive cytotoxic T-lymphocytes, stem cells, and monocytes.

A composition may be administered in intervals, and may be replenished one or more times. A composition may be administered about 1 to about 20 times. The time interval between each administration independently may be of days or even months, for example 1 month to about 6 months, or about 1 day to about 60 days, or about 1 day to about 7 days. Subsequent administration of a composition described herein can boost immunologic activity and therapeutic activity.

Timing for administering compositions is within the judgment of a managing physician, and depends on the clinical condition of the patient, the objectives of treatment, and concurrent therapies also being administered, for example. Suitable methods of immunological monitoring include a one-way mixed lymphocyte reaction (MLR) using patient lymphoblasts as effectors and tumor cells as target cells. An immunologic reaction also may manifest by a delayed inflammatory response at an injection site or implantation site. Suitable methods of monitoring of a tumor are selected depending on the tumor type and characteristics, and may include CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when an immunological or clinical benefit appears to subside, additional booster or maintenance doses may be administered.

When multiple compositions are administered to a patient, it is possible that an anti-allotype response could manifest. The use of a mixture of allogeneic cells from a plurality of donors, and the use of different allogeneic cell populations in each dose, are strategies that can help minimize the occurrence of an anti-allotype response. During the course of therapy, a subject sometimes is evaluated on a regular basis for general side effects such as a febrile response. Side effects are managed with appropriate supportive clinical care.

In some embodiments, methods and compositions provided herein are utilized to treat a cell proliferative condition. Examples of cell proliferation disorders, include, without limitation, cancers of the colorectum, breast, lung, liver, pancreas, lymph node, colon, prostate, brain, head and neck, skin, liver, kidney, and heart. Examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in Oncol./Hemotol. 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In a particular embodiment, a cell proliferative disorder is non-endocrine tumor or endocrine tumors.

Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor. Also included are pancreatic tumors (e.g., as pancreatic ductal adenocarcinomas); lung tumors (e.g., small and large cell adenocarcinomas, squamous cell carcinoma, and bronchoalveolar carcinoma); colon tumors (e.g., epithelial adenocarcinoma, and liver metastases of these tumors); liver tumors (e.g., hepatoma, cholangiocarcinoma); breast tumors (e.g., ductal and lobular adenocarcinoma); gynecologic tumors (e.g., squamous and adenocarcinoma of the uterine cervix, anal uterine and ovarian epithelial adenocaroinoma); prostate tumors (e.g., prostatic adenocarcinoma); bladder tumors (e.g., transitional, squamous cell carcinoma); tumors of the reticuloendothelial system (RES) (e.g., B and T cell lymphoma (nodular and diffuse), plasmacytoma and acute and chronic leukemia); skin tumors (e.g., malignant melanoma); and soft tissue tumors (e.g., soft tissue sarcoma and leiomyosarcoma).

A cell proliferation disorder may be a tumor in an immune semi-privileged site, such as the brain, for example. A brain tumor is an abnormal growth of cells within the brain or inside the skull, which can be cancerous or non-cancerous (benign). Benign tumors may be considered malignant only because of its location (nonresectable) in the brain. A brain tumor is any intracranial tumor having (and/or arising from) abnormal and uncontrolled cell division, often in the brain itself (neurons, glial cells (astrocytes, oligodendrocytes, ependymal cells), lymphatic tissue, blood vessels), in the cranial nerves (myelin-producing Schwann cells), in the brain envelopes (meninges), skull, pituitary and pineal gland, or spread from cancers primarily located in other organs (metastatic tumors). Primary brain tumors sometimes are located infratentorially in the posterior cranial fossa (often in children) and in the anterior two-thirds of the cerebral hemispheres or supratentorial location (often in adults), although they can affect any part of the brain. Non-limiting types of brain tumors include glioma (e.g., mixed glioma), glioblastoma (e.g., glioblastoma multiforme), astrocytoma (e.g., anaplastic astrocytoma), oligodendroglioma, medulloblastoma, ependymoma, brain stem tumors, primitive neural ectodermal tumor, pineal region tumors or tumor cells that are in the cerebrospinal fluid such as leptomeningeal gliomatosus carcinomatosus.

As certain embodiments are directed to administering a composition containing cytotoxic T cells can be administered to an immuno-privileged region of a subject, any disorder occurring in such a region can be treated. For example, a disorder of the eye, liver, testis or pregnant uterus amenable to treatment by alloreactive cytotoxic T cells can be treated with a composition of cytotoxic T cells described herein.

Certain matters are considered when compositions described herein are utilized to treat a brain tumor. If a tumor mass is resectable or partly resectable, then the composition can be administered at or near the site or in a cavity generated by the resection. If a brain tumor is completely removed it still often is beneficial to administer the composition to surrounding tissue to kill remaining cancer cells. A convenient time to administer alloactivated cells to a resectable site is during the time of surgery, in some embodiments. To keep the cells at the site until completion of the surgical procedure, it is convenient to administer the cells in a pharmaceutically compatible artificial gel, or in clotted plasma.

When the solid tumor mass is not resectable, or where less invasive procedures are desired, the composition can be injected at or near the tumor site through a needle. For deeper sites, the needle can be positioned using ultrasound, radioscintigraphy, or some other imaging technique, alone or in combination with the use of an appropriate scope or cannula. For such applications, the cell population is conveniently administered when suspended in isotonic saline or a neutral buffer in a suitable volume (e.g., about 5 to about 20 ml (e.g., 10 ml)).

EXAMPLES

The examples set forth below illustrate certain embodiments and do not limit the invention.

T lymphocytes that are transformed into cytotoxic lymphocytes (CTL) are capable of destroying brain tumor cells. When directed to destroy cells displaying non-self transplantation antigen markers known as human leukocyte antigens or HLA, they are referred to as "alloCTL." The goal of developing alloCTL is to develop a population of CTL that have strong recognition of allogeneic HLA peptides. Historically, alloCTL have been generated by one-way mixed lymphocyte reaction (MLR) where peripheral blood monocytes (PBMC) from a healthy donor are mixed with irradiated lymphoblasts from a genetically disparate individual (or patient). However, Dendritic cells (DC) are potent antigen presenting cells (APC) that display strong surface HLA.

Example 1

Sources of Responder and Stimulator Cells

For PBMC for preclinical studies IRB approvals have been obtained for: 1) normal blood donor collections at 100 ml or less, 2) purchase of buffy coats from the San Diego Blood Bank, and 3) limited leukapheresis of donors. Donors must test negative for all infectious disease agents. The density gradient isolated PBMC is washed then fractionated, using standard plastic adherence, into monocytes and lymphocytes. The nonadherent cells from the PBMC containing T, B and NK cells are either used fresh or cryopreserved in vials containing $10^7$-$10^8$ cells for the MLR generation method.

Experience using PBMC as responders indicates that the MLR can be applied equally well to fresh PBMC as well as to vitally-frozen PBMC. For LDCR, the adherent monocytes are differentiated to DC.

Example 2

Standardizing AlloCTL Generated by One-Way MLR or LDCR

Irradiated stimulator (S) lymphocytes and responder (R) lymphocytes from normal, healthy HLA-mismatched donors are collected. A small pool of young (18-50 years old) normal blood donors is employed to help standardize the PBMC reactivity to alloantigen given that PBMC from older people do not respond to antigenic stimulation as well in that they have quantitative and functional defects in the CD4 T helper cell compartment and cells that lack CD40L.

Furthermore, it was demonstrated that resting lymphocytes, activated lymphocytes (aka lymphoblasts), as well as lymphocytes or lymphoblasts that have been cryopreserved and then thawed, all have high HLA surface expression levels, thus can adequately serve as stimulators.

Example 3

Isolation and Expansion of Stimulator Lymphocytes for Sensitization of alloCTL by MLR A 100 ml blood draw from a healthy donor would be expected to yield 1 to $2 \times 10^8$ PBMC after isolation from Ficoll density gradients. After washing several times with Hank's balanced salt solution (HBSS) the PBMC are suspended in 20 ml of AIM V synthetic medium containing 5% autologous serum. The cells are injected into the extracapillary space (ECS) of the artificial capillary cartridge and perfused with medium containing Orthoclone OKT3 antibody (50 ng/$5 \times 10^7$ cells) and 240 IU/ml of rIL 2. The perfusion volume may be doubled every 2 to 4 days by adding fresh rIL 2 containing medium. Lactic acid concentration is measured daily (7 days/week, YSI Stat lactate/glucose analyzer) to determine the rate of lactate production (usually 0.2-0.25 gm/$10^9$ cells/day). Cells are fed every 4 to 5 days or when the concentration of lactate is at 0.5-0.7 gm/liter.

Lactic acid production parallels the expansion rate of the cells. Multiple vials of stimulator lymphocytes are vitally-frozen to maintain the capability of performing multiple alloCTL cultures from any given responder to stimulator (R:S) pairs; for statistical purposes multiple cultures are generated from one R:S pair. The number of stimulator PBMC frozen is based upon starting cultures at a R:S ratio of 10:1. Cells harvested from one starter culture are cryopreserved in 10% DMSO/autologous serum and stored at 80° C. The stimulator lymphocytes are thawed prior to inactivation with gamma-irradiation (127Cs-source, 2000 Rads), then washed before combining with allogeneic responder lymphocytes.

Example 4

Isolation of Monocytes and Generation of Stimulator DC

The isolation of PBMC from whole blood is by density gradient centrifugation and is washed 2× with Hank's balanced salt solution (HBSS). The PBMC are suspended at a density of $5 \times 10^6$/ml in serum-free, AIM V synthetic medium in plastic tissue culture flasks. After 30 min incubation at 37° C., the nonadherent cells containing lymphocytes are recovered and cryopreserved; the adherent monocytic cells are washed with HBSS to removed loosely adherent cells then overlaid with fresh AIM-V medium and cultivated overnight at standard conditions.

The next day the adherent cells are washed with HBSS to remove residual platelets, then overlaid with AIM-V medium supplemented with 1,000 IU/ml of GM-CSF and 500 IU/ml of rIL-4 and cultivated for 6 days to differentiate monocytes into immature DC. At day 6, the medium is supplemented with recombinant human TNF-α, IL-6 and IL-1β (10 ng/ml for each cytokine) and cultured an additional 2 days to mature the DC. An estimated approximately 10% of the starting cell number are obtained as mature DC. The DC are subjected to gamma-irradiation (127Cs-source, 2000 Rads), and washed 1× with HBSS in preparation for the LDCR protocol; these represent the stimulator DC.

Example 5

Generation of alloCTL by One-Way MLR

The generation of alloCTL by MLR is as depicted on the right side of the Flow Diagram in FIG. 1. Responder PBMC, from a donor genetically distinct from the donor supplying the stimulator cells, are isolated with Ficoll Hypaque and washed 2× with HBSS. The responder lymphocytes are combined with 127Cs-irradiated stimulator lymphocytes, at a responder to stimulator (R:S) ratio of 10:1 (i.e., one-way MLR). They are placed into the artificial capillary cartridges and cultivated at 37° C. with 5% CO2 with AIM V medium containing 5% autologous serum and 60 International Units (IU)/ml of rIL 2 for 14 days; the cells over a 7 10 day period are weaned from serum containing medium.

A restimulation of the alloCTL occurs, if growth patterns indicate it is necessary, at day 12 post-MLR with relevant lymphoblasts at a R:S of 10:1. Cytotoxicity assessments, proliferation, phenotypically-defined cytotoxic subsets and cytokine production is determined on day 14 post-MLR cells.

Example 6

Generation of alloCTL by One-Way LDCR

The generation of alloCTL by LDCR is as depicted on the left side of the Flow Diagram shown in FIG. 1. The allodonors used for responders or pCTL are HLA-disparate to the donor supplying stimulator cells. The adherent cells are grown with growth factors that encourage DC (immature) growth. Growth factors are then added to the culture medium to mature the DC. Briefly, the plastic adherent monocytic cells are cultured in serum free AIM-V medium supplemented with 1000 units/ml rhGM-CSF and 500 units/ml rhIL-4 at 37° C. in a humidified, 5% CO2 incubator. Six days later, the immature DC are stimulated with recombinant human TNF-α, IL-6 and IL-1β (10 ng/ml for each cytokine) to induce their maturation for 2 days. DCs are harvested, irradiated and combined with responder PBMC for LDCR at a R:S ratio of 10:1.

The DC present peptides from alloantigen (i.e., stimulators) to the T lymphocytes of the allodonor in the presence of low dose IL-2 (60 IU/ml). Reactive responder lymphocytes develop into alloCTL capable of recognizing the HLA on the stimulator cells over a 12 day period. They are restimulated with DC at a 10:1 R:S on day 12 post-LDCR and assessed 2 days later in 4 hour 51Cr-release cytotoxicity assays, for proliferation, and for phenotype and cytokine production.

Example 7

Chromium Release Cytotoxicity Assays

AlloCTL preparations are generated from the same R:S pairs by either MLR or by LDCR. The cytotoxicity of the alloCTL to relevant target, i.e., stimulator lymphoblasts displaying the HLA to which they are sensitized, is then determined. 51Cr-release assays are used determine the lytic activity of alloCTL effector cells when they are co-incubated with the target cells. Four hour assays are run in 96-well plates at multiple effector to target (E:T) ratios of 3:1, 10:1, 30:1 with triplicate samples as previously described. Percent specific release is calculated by the formula: $[(cpm_{experimental} - cpm_{spontaneous})/(cpm_{maximal} - cpm_{spontaneous})] \times 100\%$. Spontaneous release is measured for targets in assay medium alone and maximal release is produced by lysis of the targets with 2% Triton X-100 (Sigma, St. Louis, Mo.). Lysis obtained at each given E:T ratio is determined and the thresholds of low, moderate and high cytotoxicity can be defined accordingly.

Day 14 alloCTL generated by 1-way MLR and 1-way LDCR are compared. Statistical assessment of lytic activity and the effects of reaction type (MLR vs LDCR), the three E:T ratios evaluated as an ordered factor, the samples, and their possible interactions are made by ANOVA with planned post-hoc comparisons. All statistical operations are accomplished in R, version 2.9 or higher. Optimization of alloCTL by DC presentation is considered possible if the cytotoxic responses, by DC-generated alloCTL compared to 1-way MLR generated alloCTL, against stimulator lymphoblast target cells is >15% higher when all data are grouped and normalized from three equivalent E:T ratios tested.

The alloCTL preparations have the ability to elicit alloantigen-specific immune responses against relevant target cells in vitro. Target cells are OKT3 or PHA-stimulated lymphoblasts, which display high levels of HLA antigen. "Relevant" targets are the lymphoblasts derived from stimulator PBMC. Responding donor lymphoblasts express HLA that should be regarded as "self" and therefore should not be targets of the alloreactive T cells. They are used as a background, negative control. Additionally, K562 natural killer (NK)-sensitive cell targets do not express HLA antigen and are used as "irrelevant" target cells to assess nonspecific injury caused by NK cells (non-MHC-restricted killing) that is unrelated to T-cell alloreactivity (MHC-restricted killing). Lysis of K562 is subtracted from stimulator lymphoblast lysis for these comparisons also. The levels of HLA expression by lymphoblasts is analyzed by flow cytometry using the pan HLA-ABC antibody (W6/32) to assess whether the cytotoxicity directly relates to the relative antigen density (MFIs) of HLA on the relevant target cells.

Example 8

Phenotypic Characterization of Activated, Mature Dendritic Cells

Aliquots of DC are stained with monoclonal antibodies (mAbs) against DC surface markers (anti-HLA class I conjugated to fluorescein isothiocyanate (FITC), anti-HLA class II DR conjugated to PerCp, anti-CD11c conjugated to APC, anti-CD80, anti-CD83, and anti-CD86 conjugated to phycoerythrin (PE) (BD Biosciences/Pharmingen, San Diego, Calif.) on ice for 1 hour. The cells are washed three times with cold PBS before analyzing on an LSR II flow cytometer.

Example 9

Phenotypic Characterization of Activated, CD3 Cytotoxic T Cell Subsets by Flow Cytometric Analyses The cytotoxic subsets with alloCTL preparations for production of IFN-γ are examined. This cytokine has previously been shown to be most relevant to the Th1 cell-mediated responses to immunotherapy exhibited by T lymphocytes. Additionally, IFN-γ has been used as an in vitro monitoring tool to predict GVH in renal transplant patients where slight mismatches in donor to patient HLA are expected.

AlloCTL preparations generated from the same responder/ stimulator pairs by MLR or by LDCR are used to determine the fold-increase in the phenotypically-defined CD3/CD8 cytotoxic subset displaying the activated T cell marker (CD69) that produces IFN-γ within the alloCTL upon exposure to relevant target, i.e., stimulator patient lymphoblasts displaying the HLA to which they are sensitized. The cell subset positive for CD3, CD8, CD69, and intracellular IFN-γ (BD Fast Immune Kit, BD Biosciences) is assessed at 24 hr after incubation with or without relevant target cells (stimulator lymphoblasts at a R:S of 10:1). In the last 6 hr of the 24 hr incubation, 10 μg/ml of Brefeldin A, a secretion inhibitor, is added. Nonstimulated or stimulated alloCTL are each aliquoted into three tubes ($10^6$ cells/tube) and pelleted at 100×g. Flow cytometric analysis is performed, staining for cell surface markers (e.g., CD3+, CD8+, CD69+) and cytoplasmic IFN-γ cytokine expression. The Fix and Perm reagents are used where indicated according to the manufacturer's protocol. In brief, alloCTL cell pellets are resuspended and incubated with a fluorochrome-conjugated monoclonal antibody (mAb) cocktail on ice for 30 minutes. The cells are washed, fixed and permeabilized, then incubated with a fluorochrome-conjugated mAb specific for IFN-γ for 30 min. Following the second antibody incubation, the cells are washed again and resuspended in PBS and analyzed by flow cytometry. The analyses is performed with a six-color capable BD LSR II flow cytometer. Percentages of the positive activated T cell subset and the mean fluorescence intensities (MFI) of IFN-γ are obtained.

The fold increases in the percentages of the activated subset in the alloCTL that are restimulated versus those not are determined. As well, the fold increases in the MFIs for IFN-γ in the alloCTL subsets that are or are not restimulated are determined. Each of these measures may be usefully predictive of the extent of cytolysis. An increase in the cytotoxic subset or the degree of IFN-γ expression that is >1.5-fold may reach significance based upon other observations with patient PBMC in vaccine trials for gliomas. Other investigators' data collected by this flow cytometric method compare well to that collected by limiting dilution analyses.

Example 10

Determination of the Proliferative Response of the alloCTL Made by MLR or DC Presentation Upon their Exposure to Relevant Stimulator Lymphoblasts The CTL precursor frequency within a donor mononuclear cell pool to patient HLA antigens is variable. It may be as high as 10% to allogeneic MHC antigen or as low as 0.1-0.01%. Anticipating that the precursor CTL frequency is identical in any given responder/stimulator pair, DC presentation is compared to T lymphocyte presentation in an MLR for enhancing the proliferative events of alloresponders.

The overall intent is to generate therapeutically significant quantities of alloCTL. The ability of T cells to proliferate when exposed to the antigens to which they are sensitized has been used as an indicator of the presence of antigen-specific CD4+ helper T cells.

The proliferative response of the alloCTL preparations upon their exposure to relevant patient lymphoblasts displaying the HLA to which they are sensitized is characterized. The proliferative response of the alloCTL upon their exposure to relevant stimulator lymphoblasts is determined for alloCTL preparations generated from the same R:S pairs made by MLR or by LDCR and converted to stimulation indices for comparison.

The capacity to proliferate in response to HLA presentation by relevant stimulator cells is measured by tritiated thymidine uptake at a R:S ratio of 10:1. In response to the alloCTL seeing relevant antigen, proliferation should ensue. After 48 hr, the culture is pulse-labeled with 3H-thymidine. DNA synthesis, as a measure of proliferation, is quantified by using a liquid scintillation counter to measure the amount of radiolabeled thymidine incorporated into the DNA. A stimulation index (SI) is calculated by dividing the number of cpm for the resensitized alloCTL by the number of cpm for the cells incubated without sensitizing cells.

The SIs obtained for each alloCTL preparation can be categorized as having a high proliferative population versus a low proliferative population. The in vitro proliferative capacity of the alloCTL can thereby be compared to their cytotoxicity, phenotypic analyses, and the level of HLA mismatch between the responder and stimulator.

In general, while there is some consensus in the literature that proliferative events correlate with responder/stimulator MHC disparities at Class II, while cytolytic activity is a function of disparities at Class I, the separation of proliferative and cytolytic functions should be confirmed by analyzing the data with molecular HLA types of the responder and stimulator. This is to be addressed using both conventional and robust regression analyses.

In addition to comparing the proliferative differences in alloCTL generated by MLR vs LDCR methods, proliferation of the alloresponder enriched cultures at restimulation results from HLA Class II disparities should be discerned, whereas the functionality of the cells as determined by cell injury, and cytotoxic cell phenotype/cytokine production, relates to HLA Class I disparities between responder and stimulators.

Example 11

Determination of the Soluble Th1 to Th2 Cytokine Ratios Produced Upon alloCTL Exposure to Relevant Target Other researchers have compared IFN-γ/IL-10 ratios as an in vitro monitoring tool for assessing tumor host response using PBMC pre- and post-vaccination, and for T cell induced GVH development and rejection in transplant patients. Here the soluble Th1 to Th2 (i.e., IFN-γ to IL-10 or TNF-α to IL-4) cytokine ratios produced upon alloCTL exposure to relevant stimulator target are determined with alloCTL preparations generated from the same R:S pairs by MLR or by LDCR. Higher Th1 to Th2 ratios may correlate with induction of a proinflammatory response in vivo and/or correspond to better cytolysis to relevant target.

Supernatants from alloCTL coincubated for 24 hr in the presence or absence of relevant irradiated stimulator lymphoblasts are examined. The cell suspensions are clarified by refrigerated centrifugation at 400×g for 10 min. The clarified medium, or dilutions of it if necessary, are analyzed using the BD cytometric bead array system. The cytokines tested include Th1 and Th2 cytokines: IL-2, IL-4, IL-5, IL-10, gamma interferon (γ-IFN) and tumor necrosis factor alpha (TNF-α). The array system allows for collection of multiple cytokine results from a single small sample at relatively sensitive levels of detection (2.0-4.0 μg/ml). Therefore, not only IFN-γ/IL-10 ratios but other alternative Th1/Th2 cytokine permutations (i.e., TNF-α/IL-4) as well are analyzed. For this reason, the array can be considered a cost effective alternative to ELISAs specific for the four cytokines.

Statistical Evaluation. Statistical analysis is performed using conventional and statistically robust techniques with the R statistical package. Data descriptions include standard 5-point summaries as well as the first four moments and MAD (median absolute deviations). To elucidate the interrelationships of functional alloresponsiveness (i.e., cytotoxicity of the alloCTL, fold-increases in the phenotypic subset displaying the activated T cell marker, proliferation in response to exposure to relevant antigens and/or proinflammatory cytokine production) relative to HLA mismatch, correlative studies include both pairwise analyses with confidence intervals and additional analyses to investigate systematic nonlinearities. Both conventional ANOVA and its robust analogues are used to investigate the relationships. The mean averages of triplicate samples are compared in three separate experiments using the same R:S pairs. The higher the number of alloCTL preparations made by both methods, the better the statistic will be. The number of experiments needed depends upon the pilot data and power analyses. The implication to obtaining significantly higher cytotoxic assessments with alloCTL generated by LDCR vs MLR is that an alteration of the generation method for alloCTL for clinical studies could be made by amending the existing IND to the FDA.

Example 12

Validation Using Patient Tumor/Lymphocyte Sets as Targets and Stimulator of alloCTL A tissue bank that contains matched patient lymphocyte and glioma specimens could be used for validation purposes. Tissues in the bank are obtained from patients by IRB-approved protocols. The patient lymphocytes act as stimulators of alloCTL. The cultured glioma specimens act as relevant targets in cytotoxicity assays. It has been documented that tumor cells in situ and in culture express MHC class I antigens.

Functional characteristics of alloCTL generated by MLR and by LDCR are compared, including selective cytotoxicity toward relevant HLA-bearing targets, and in response to incubation with relevant target cells, upregulation of proinflammatory cytotoxic subsets, Th1 cytokine production, and proliferation.

Final Considerations

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A composition administrable to a patient, comprising: alloreactive cytotoxic T cells,
   wherein the alloreactive cytotoxic T cells have been produced from cells of a donor that is partially human leukocyte antigen (HLA) disparate with the patient, and wherein the cytotoxic T cells have been activated to recognize a predetermined cell type in the patient.

2. The composition of claim 1, wherein the alloreactive cytotoxic T cells have been activated to recognize a predetermined cell type in the patient by displaying alloresponsiveness to HLA determinants present on the patient's cells.

3. The composition of claim 1, wherein the alloreactive cytotoxic T cells have been activated to recognize peptides derived from HLA.

4. The composition of claim 3, wherein the alloreactive cytotoxic T cells have been activated to recognize a HLA antigen of the patient.

5. The composition of claim 3, wherein the alloreactive cytotoxic T cells have been contacted with matured dendritic cells from the patient.

6. The composition of claim 5, wherein the dendritic cells have been matured by exposure to cytokines with or without one or more pathogen-associated molecular pattern (PAMP) molecules.

7. The composition of claim 5, wherein the dendritic cells from the patient have been inactivated.

8. The composition of claim 5, wherein the dendritic cells have been derived from monocytes of the patient.

9. The composition of claim 3, wherein the patient has cancer.

10. The composition of claim 9, wherein the cancer is a tumor located in an immune-privileged site.

11. The composition of claim 10, wherein the tumor is located in the brain.

12. The composition of claim 1, wherein to recognize a predetermined cell type in the patient comprises to display alloresponsiveness to HLA determinants present on the patient's cells.

* * * * *

UNITED STATES PATENT AND TRADEMARK OFFICE
CERTIFICATE OF CORRECTION

| | | |
|---|---|---|
| PATENT NO. | : 8,586,359 B2 | Page 1 of 1 |
| APPLICATION NO. | : 12/844516 | |
| DATED | : November 19, 2013 | |
| INVENTOR(S) | : Carol A. Kruse | |

It is certified that error appears in the above-identified patent and that said Letters Patent is hereby corrected as shown below:

Title Page, Assignee Item (73): Replace --Promising Furture, LLC-- with --Promising Future, LLC--.

Signed and Sealed this
Eleventh Day of February, 2014

Michelle K. Lee
*Deputy Director of the United States Patent and Trademark Office*